(12) United States Patent
Xu et al.

(10) Patent No.: US 6,426,194 B1
(45) Date of Patent: Jul. 30, 2002

(54) HOMOGENEOUS ENZYMATIC ASSAY FOR VITAMIN B6 AND IMPROVEMENTS IN H2S DETECTION

(75) Inventors: Mingxu Xu; Qinghong Han; Yuying Tan, all of San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 0 days.

(21) Appl. No.: 09/495,889

(22) Filed: Feb. 1, 2000

Related U.S. Application Data

(63) Continuation-in-part of application No. 09/340,991, filed on Jun. 28, 1999, now Pat. No. 6,066,467.
(60) Provisional application No. 60/118,031, filed on Feb. 1, 1999.

(51) Int. Cl.[7] .............................. C12Q 1/37; C12Q 1/00; C12Q 1/48; C12Q 1/52; C12Q 33/53
(52) U.S. Cl. .............................. 435/24; 435/4; 435/968; 435/15; 435/16; 435/975
(58) Field of Search .............................. 435/24, 4, 968, 435/15, 16, 975

(56) References Cited

U.S. PATENT DOCUMENTS

| | | | |
|---|---|---|---|
| 4,940,658 A | 7/1990 | Allen et al. | 435/23 |
| 5,438,017 A | 8/1995 | Allen et al. | 435/23 |
| 5,478,729 A | 12/1995 | Van Atta et al. | 435/7.93 |
| 5,631,127 A | 5/1997 | Sundrehagen | 435/4 |
| 5,827,645 A | 10/1998 | Sundrehagen et al. | 435/4 |
| 5,985,540 A | 11/1999 | Tan et al. | 435/4 |
| 5,998,191 A | 12/1999 | Tan et al. | 435/232 |
| 6,066,467 A | * 5/2000 | Xu et al. | 435/23 |

FOREIGN PATENT DOCUMENTS

| | | |
|---|---|---|
| WO | WO 93/15220 | 8/1993 |
| WO | WO 98/07872 | 2/1998 |
| WO | WO 98/14562 | 4/1998 |
| WO | WO99/05311 | 2/1999 |

OTHER PUBLICATIONS

Argoudelis, C.J.; Chromatogr., V526(1), pp. 25–33, (1990) Abstract Only).*
Inagaki et al; Progress In Clinical & Biological Research; V144A, pp. 355–363 (1984), (Abstract Only).*
Araki et al., "Determination of Free and Total Homocysteine in Human Plasma by High–Performance Liquid Chromatography with Fluorescence Detection," *Journal of Chromatography* (1987) 422:43–52.
Bagnara et al., "Molecular Characterisation of Adenosylhomocysteinase from *Trichomonas vaginalis*," *Molecular and Biochemical Parasitology* (1996) 81:1–11.
Briggs, M., Ed. *Vitamins in Human Biology and Medicine*, Boca Raton, FL, CRC Press, Inc. (1981) (Table of Contents Only).
Brown, M. L., ed. *Present Knowledge in Nutrition*. 6th ed. Washington, D.C., International Life Sciences Institute–Nutrition Foundation (1990) (Table of Contents Only).

(List continued on next page.)

*Primary Examiner*—Louise N. Leary
(74) *Attorney, Agent, or Firm*—Morrison & Foerster LLP

(57) ABSTRACT

Enzymatic methods to determine the concentration of pyridoxal 5'-phosphate (PLP) in biological fluids are described. The methods of the invention are useful to assess risk for cardiovascular disease. The assay can be a homogeneous assay using the ability of PLP to function as a co-enzyme for homocysteinase and related enzymes and measuring the products of the reaction preferably spectrophotometrically. The invention also includes improvements in sensitivity of assays for measuring hydrogen sulfide production by measuring fluorescence as opposed to absorbance of the oxidized product of $H_2S$ with N,N-dialkyl p-phenylene diamine.

20 Claims, 5 Drawing Sheets

OTHER PUBLICATIONS

Dudman et al., "Assay of Plasma Homocysteine: Light Sensitivity of the Fluorescent 7–benzo–2oxa–1, 3–Diazole–4–Sulfonic Acid Derivative, and Use of Appropriate Calibrators," *Clinical Chemistry*(1996) 42 (12):2028–2032.

Esaki et al., "L–Methionine γ–Lyase from *Pseudomonas putida* and Aeromonas,"*Methods in Enzymology* (1987) 143:459–465.

Gage et al., "A New Route for Synthesis of Dimethylsulphoniopropionate in Marine Algae," *Nature* (1997) 387:891–893.

Garg, Short–term and Long–term Variability of Plasma Homocysteine Measurement, *Clinical Chemistry* (1997) 43(1):141–145.

Gilfix et al., Novel Reductant Determination of Total Plasma Homocysteine, *Clinical Chemistry* (1997) 43(4):687–688.

Hoffman et al., "Diagnosis and Treatment of Homocysteine Disease Using Recombinant Homocysteinase" 2nd International Conference on Homocysteine Metabolism, Nijmegen, Netherlands, Apr. 26–29, 1998. Ne*therlands Journal of Medicine* 52 (SUPPL) 1998. S41. ISSN: 0300–2977, XP002087823.

Hori et al., "Gene Cloning and Characterization of Pseudomonas putida L–Methionine–α–Deamino–γ–Mercaptomethane–Lyase", *Cancer Research* (1996) 56 : 2116–2122.

Inoue et al., "Functional Analysis of the γ–Glutamylcysteine Synthetase of *Escherichia coli B:*Effect of Substitution of His–150 to Ala," *Applied Microbiology and Biotechnology* (1993) 38:473–477.

Ito et al., "Purification and Characterization of Methioninase from *Pseudomonas putida,*" *Journal of Biochemistry* (1976) 79:1263–1272.

Jakubowski et al., "Synthesis of Homocysteine Thiolactone by Methionyl–tRNA Synthetase in Cultured Mammalian Cells," *FEBS Letters* (1993) 317(3):237–240.

Kang et al., "Hyperhomocyst(e)inemia as a Risk Factor for Occlusive Vascular Disease," *Annual Review of Nutrition* (1992) 12:279–298.

Kerr, "Life Goes to Extremes in the Depp Earth–and Elsewhere?, " *Science* (1997) 276:703–704.

Lockwood et al., "Purification and Characterization of Methionine γ–Lyase from *Trichomonas vaginalis,*" *Biochemical Journal* (1991) 279:675–682.

Markos et al., "Primary Stucture of a Cytosolic Malate Dehydrogenase of the Amitochondriate Eukaryote, *Trichomonas vaginalis,*" *FEMS Microbiology Letters* (1996) 135:259–264.

McCully, "Vascular Pathology of Homocysteinemia: Implications for the Pathogenesis of Arteriosclerosis," *American Journal of Pathology* (1969) 56:111–128.

McCully, "Chemical Pathology of Homocysteine I. Atherogenesis," *Annals of Clinical and Laboratory Science* (1993) 23(6):477–493.

McCully, "Chemical Pathology of Homocysteine II. Carcinogenesis and Homocysteine Thiolactone Metabolism," *Annals of Clinical and Laboratory Science* (1994) 24(1):27–59.

McCully, "Chemical Pathology of Homocysteine III. Cellular Function and Aging," *Annals of Clinical and Laboratory Science* (1994) 24(2):134–152.

McCully, "Homocysteine and Vascular Disease," *Nature Medicine* (1996) 2(4):386–389.

McKie et al., "The Primitive Protozoon Trichomonas vaginalis Contains Two Methionine γ–Lyase Genes that Encode Members of the γ–Family of Pyridoxal 5'–Phosphate–Dependent Enzymes," *The Journal of Biological Chemistry* (1998) 273:5549–5556.

Mottram, *Gene Bank,* (Jul. 17, 1997), Accession No. AJ000486, NID g23300884; and Accession No. AJ000487, NID g2330886.

Mudd et al., "The Natural History of Homocystinura Due to Cystathionine β–Synthase Deficiency," *American Journal of Human Genetics* (1985) 37:1–31.

Nygard et al., "Plasma Homocysteine Levels and Mortality in Patients with Coronary Artery Disease," *The New England Journal of Medicine* (1997) 337(4):230–236.

Pennist, "In Industry, Extremophiles Begin to Make Their Mark," *Science* (1997) 276:705–706.

Reynolds, "Nationwide Assay ov Vitamin B6 in Human Plasma by Different Methods," *Fed Proc* Abst. No. 2185 (1983) 42:665.

Riley et al., "Rapid and Practical DNA Isolation from Trichomonas vaginalis and Other Nuclease Rich Protozoa," *Molecular and Biochemical Parasitology* (1992) 51:161–164.

Robinson et al., "Homocysteine and Coronary Artery Disease," *Cleveland Clinic Journal of Medicine* (1994) 16(6):438–450.

Selhub et al., "Association Between Plasma Homocysteine Concentrations and Extracranial Carotid–Artery Stenosis," *New England Journal. of Medicine* (1995) 332:286–291.

Shipchandler et al., "Rapid, Fully Automated Measurement of Plasma Homocyst(e)ine with the Abbott IMx®Analyzer," *Clinical Chemistry* (1995) 41(7):991–994.

Stampfer et al., "A Prospective Study of Plasma Homocyst(e)ine and Risk of Myocardial Infarction in US Physicians," *Journal of the American Medical Association* (1992) 268:877–881.

Tan et al., "Overexpression and Large–Scale Production of Recombinant L–Methionine–α–Deamino–γMercaptomethane–Lyase for Novel Anticancer Therapy," *Protein Expression and Purification* (1997) 9:233–245.

Tanaka et al., "Selective Determination of L–Methionine and L–Cysteine with Bacterial L–Methionine γ–Lyase and Antitumor Activity of the Enzyme," *Journal of Applied Biochemistry* (1980) 2:439–444.

Tanaka et al., "Properties of L–Methionine γ–Lyase from Pseudomonas ovalis," *Biochemistry* (1977) 16:100–106.

Thong et al., "Trichomonas Species: Homocysteine Desulphurase and Serine Sulphydrase Activities," *Experimental Parasitology* (1987) 63:143–151.

Thong et al., "Homocysteine Desulphurase Activity in Trichomonads," *IRCS Journal of Medical Science* (1985) 13:493–494.

Thong et al., "L–Serine Sulphydrase Activity in Trichomonads," *IRCS Journal of Medical Science* (1985) 13:495–496.

Thong et al., "L–Methionine Catabolism in Trichomonads," *Molecular and Biochemical Parasitology* (1987) 23:223–231.

Ueland et al., "Plasma Homocysteine and Cardiovascular Disease," in *Atherosclerotic Cardiovascular Disease, Hemostasis and Endothelial Function,* Francis, R.B. Jr., Ed., Marcel Dekker, Inc , New York (1992) pp. 183–236.

Vilaseca et al., "Total Homocysteine in Pediatric Patients," *Clinical Chemistry* (1997) 43(4):690–691.

Watanabe et al., "The Nucleotide Sequence of the Gene for γ–Glutamylcysteine Synthetase of *Escherichia coli*", *Nucleic Acids Research* (1986) 14(11):4393–4400.

Wolfe et al., "Grazing–Activated Chemical Defence in a Unicellular Marine Alga," *Nature* (1997) 387:894–897.

Yamaguchi et al., "Microfluorometric Assay for Methionine with Novel Enzyme L–Methionine γ–Lyase," *Annual Report of Sapporo City Institute of Public Health* (1993) 20:67–74 (with Translation).

Zuo et al., "Uptake of Amino Acids by the Parasitic, Flagellated Protist *Trichomonas vaginalis,*" *Microbiology* (1995) 141:2637–2642.

* cited by examiner-

HOMOGENEOUS ENZYMATIC ASSAY FOR VITAMIN B6 AND IMPROVEMENTS IN H2S DETECTION

CROSS-REFERENCE TO RELATED APPLICATIONS

This application is a continuation-in-part of U.S. Ser. No. 09/340,991 filed Jun. 28, 1999, now 6,066,467 the contents of which are incorporated herein by reference. It also claims priority from provisional application Serial No. 60/118,031 filed Feb. 1, 1999.

TECHNICAL FIELD

The invention concerns an assay for Vitamin $B_6$, the active form of which is pyridoxal 5'-phosphate and to improvements in detection of $H_2S$ by using fluorescence. More specifically, the invention concerns kits and methods for determining pyridoxal phosphate concentrations in biological fluids using the apoenzyme of a homocysteinase. It also concerns improving the sensitivity of such assays and assays for homocysteine as well by measuring the fluorescence of a complex generated by the reaction of $H_2S$ with a dialkyl phenylene diamine and an oxidizing agent.

BACKGROUND ART

PCT publication WO 99/05311 describes high specificity homocysteine assays in biological samples using a homocysteinase enzyme with high specificity for homocysteine in comparison to cysteine sufficient for biological fluid levels. This permits the measurement of the common product, $H_2S$, generated by these enzymes both from cysteine and homocysteine as a valid measure of homocysteine per se in physiological fluids. The $H_2S$ generated can be measured in a variety of ways as described in that application. It has now been found that the sensitivity of this assay can be improved by measuring the fluorescence of the complex formed by hydrogen sulfide with the chromogenic reagents and an N,N-dialkyl p-phenylene diamine and an oxidizing agent such as potassium ferricyanide. The resultant, 3,7-(bis dialkylamino)phenothiazine-5 chloride can be measured by absorbance or by excitation and measurement of fluorescence.

This measurement of fluorescence is also useful in the assay herein described for pyridoxal 5'-phosphate.

Pyridoxal 5'-phosphate (PLP) is the biologically active form of Vitamin $B_6$. PLP is a cofactor for many essential enzymes involved in amino acid metabolism and fatty acid metabolism, including methioninase and homocysteinase. Additional enzymes for which PLP is the prosthetic group include glycogen phosphorylase as well as all aminotransferases. PLP is also involved in decarboxylations, deaminations, racemizations, transaminations and aldol cleavages at the α-carbon atom of amino acids. These enzymes depend on PLP in order to be active, so PLP is an important metabolic factor. PLP is derived from Vitamin $B_6$; Vitamin B6 is not synthesized by most mammals, including humans. Therefore, this vitamin is most commonly supplied in the diet. Epidemiological studies have shown that PLP deficiency is the strongest nutritional correlate to mortality from cardiovascular diseases. Deficiency of Vitamin $B_6$ results in symptoms such as dermatitis and nervous disorders.

Given the involvement of PLP in metabolism and its deficiency in various disease states, multiple methods for the determination of Vitamin $B_6$ levels and $B_6$ status are known in the art.

Microbiological assays using *Saccharomyces carlsbergensis* (*S. uvarum*), *Streptococcus faecium,* and *Lactobacillus casei* have been used to measure the various forms of $B_6$ in blood and urine. Fluorometric assays of urinary 4'-pyridoxic acid and blood PLP after conversion to a cyanide complex or condensation with a fluorophore, such as methyl anthranilate followed by reduction are also used. 4'-Pyridoxic acid can also be determined by HPLC. The PLP concentration in plasma is also measured by determining the formation of radioactively labeled tyramine from labeled tyrosine using the apoenzyme form of tyrosine decarboxylase. The reference interval is 5 to 30 ng/ml of plasma (Reynolds, R. D., *Fed. Proc.* (Abst. No. 2185) (1983) 42:665). This form of assay is also available commercially as an "ALPCO" kit from American Laboratory Products Company, Ltd. (Windham, N.H. 03087).

Blood transaminases have been used as an indicator of Vitamin $B_6$ status. The enzyme activity in serum is depressed in $B_6$ deficiency. However, release of these enzymes reflects cell death, and breakdown in various tissues causes variability. Erythrocyte levels of aspartate and alanine aminotransferases provide a better indication of Vitamin $B_6$ status (Briggs, M., Ed. *Vitamins in Human Biology and Medicine,* Boca Raton, Fla., CRC Press, Inc., 1981).

Measurement of urinary tryptophan metabolites, such as xanthurenic acid, following an oral loading (2–5 g) of L-tryptophan have also been used to indicate $B_6$ status. Amounts of xanthurenate above the normal (25 mg/d) level indicate Vitamin $B_6$ deficiency. A methionine loading test has also been utilized (Briggs, M., op. cit., Brown, M. L., Ed. *Present Knowledge in Nutrition.* $6^{th}$ ed. Washington, D.C., International Life Sciences Institute-Nutrition Foundation, 1990). The ratio of cystathionine to cysteine sulfinic acid measured by amino acid analysis is elevated in a 24-h urine of $B_6$-deficient patients after a 3-g methionine load.

Given the increasing awareness of the role of Vitamin $B_6$ in cardiovascular disease, and the public health goal to screen patients for risk from cardiovascular disease, there is a critical need for more convenient and reliable analytical procedures that can be used to determine PLP/Vitamin $B_6$ levels in patients. Such procedures are expected to provide considerable medical benefit both in those cases where decreased PLP/Vitamin $B_6$ concentrations place an individual at risk for a particular disease state, and in cases where decreased PLP/vitamin $B_6$ concentrations are a detectable byproduct of an existing disease state.

Such analytical procedures would provide great benefit by predicting a patient's susceptibility to cardiovascular disease before onset can be detected by other procedures. In this regard, great benefit would be achieved by adapting such procedures to the widespread screening of the general population, and in particular, to patients otherwise suspected of being at risk for cardiovascular disease. It is therefore critically important that the assay be convenient to use, simple, and inexpensive. The present invention provides such methods, including diagnostic kits for use in the clinical setting.

DISCLOSURE OF THE INVENTION

The invention provides assays capable of detecting PLP levels in a biological sample fluids such as urine, tissue fluid, blood, whole blood, blood serum or blood plasma from a subject. The methods of the invention are thus useful to assess risk for cardiovascular disease. The invention methods also include methods of determining results which are useful not only in methods to determine PLP/$B_6$, but also in assay methods which assess the production of $H_2S$ as a product and measure of the desired analyte using chromogenic reagents.

In one aspect, the invention is directed to a method for determining the amount of PLP in a biological sample which method comprises contacting said sample with the apoenzyme form of a PLP-requiring enzyme which can generate a product when PLP is present preferably one that is determinable by color or fluorescence. Thus, preferred apoenzymes of the invention are homocysteine/methionine alpha-gamma lyases which have been depleted of the normally associated PLP. Also preferred are such enzymes which generate hydrogen sulfide from cysteine. These enzymes generate products which are readily detectable by colorometric or fluorometric means when the enzymes are restored/activated to the holoenzyme form. The sensitivity of the assay is greatly multiplied by the function of the PLP as a co-factor; high levels of substrate can therefore be used and high levels of product generated.

In another aspect, the invention is directed to a method to improve the sensitivity of detection of $H_2S$ generated in assays, such as assays for homocysteine, which generate hydrogen sulfide, which method comprises measuring the fluorescence of the product of hydrogen sulfide with a dialkyl p-phenylene diamine and an oxidizing agent such as a ferricyanide. This improvement is especially important in assays for homocysteine or cysteine per se as the sensitivity of the assay is enhanced over one hundred fold. However, this method may also be used in assays for PLP where, because of the multiplying effect of the co-enzyme action of PLP, enhanced sensitivity is not so important.

In other aspects, the invention is directed to diagnostic kits for the methods of the invention.

MODES FOR CARRYING OUT THE INVENTION

Figure 1:
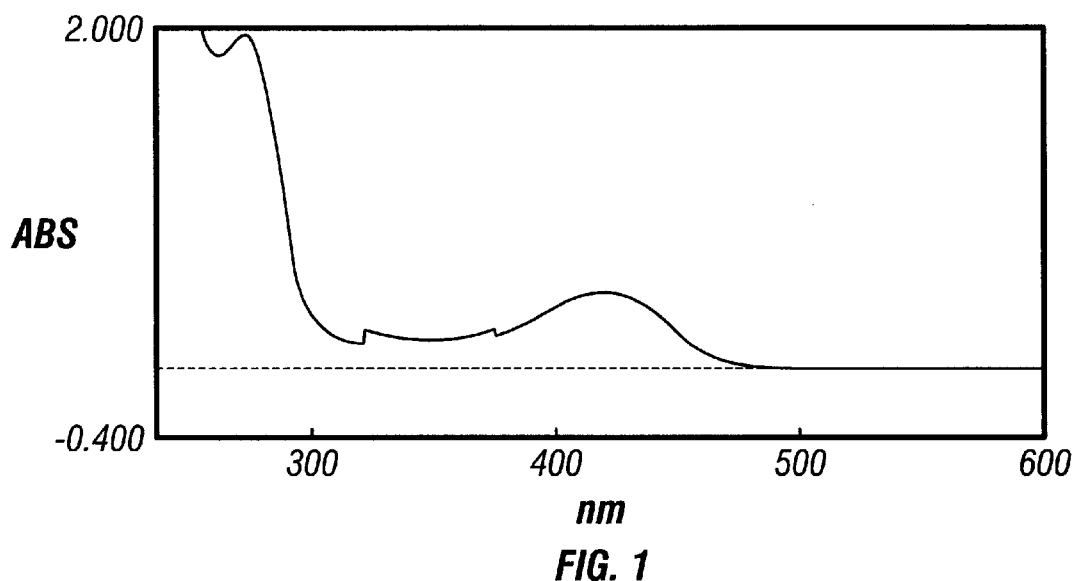
FIG. 1 shows the spectrum of homocysteine alpha, gamma lyase cloned from *Trichomonas vaginalis* before treatment with hydroxylamine.

Lowered PLP/vitamin levels are recognized as a risk factor for cardiovascular disease. The present invention is directed to PLP/Vitamin $B_6$ assay procedures, and reagents therefor, that permit direct an convenient determination of PLP/Vitamin $B_6$ concentrations in a biological sample. According to the practice of the invention, PLP/Vitamin $B_6$ concentrations in biological samples are determined enzymatically with apoenzymes forms of PLP requiring enzymes hereinafter referred to as "apoenzymes". The level of PLP in the sample determines restoration of their corresponding holoenzyme activity, thus determining PLP/Vitamin $B_6$ concentrations in a given sample by detection of the enzymatic activity upon contact with an appropriate substrate. Preferred apoenzymes are those forms of methioninase/ methioninase/cysteinase which catalyze the breakdown of these amino acids. It is preferred to detect product hydrogen sulfide, although product ammonia and/or conversion products such as alpha-ketobutyrate or other products may also be detected.

With regard to methioninase and homocysteinase, one nmole of enzyme is equivalent to 172 $\mu$g of enzyme which is equivalent to approximately 10 units of enzyme. Since the methioninase or homocysteinase holoenzyme binds 1 PLP per subunit or 4 PLP per tetramer, only 4 nmoles PLP can activate 1 nmole of enzyme equivalent to 10 units of enzyme. Ten units of enzyme will give an OD or 10 or more in the presence of 10 mM homocysteine or methionine measured by the methylene blue principle, by lead sulfide formation from lead acetate, or by formation of $\alpha$-ketobutyrate using the MBTH assay. Serum levels of $B_6$ induce a catalysis of $10^{-2}$ M homocysteine or methionine, an amplification of $10^7$.

The signal from the restored/activated holoenzyme is of sufficient strength that a homogeneous clinical chemistry diagnostic is feasible. Spectrophotometric detection is the most convenient detection method. By "detecting a product spectrophotometrically" is meant that the product is either colored or fluorescent. The spectrophotometric detection may be with the naked eye or may use an instrument such as a spectrophotometer or fluorometer. The assay is also of sufficient sensitivity that a dry chemistry test, such as by the use of a dipstick upon which the apoenzyme is immobilized, may be used to detect PLP in serum or urine. In a preferred embodiment of the invention, the resident PLP of homocysteinase and methioninase is gently removed by contact with hydroxylamine to result in apoenzymes that can later re-bind PLP to restore activity. For example, such apoenzymes are immobilized on filter paper, such as on a dipstick, which apoenzymes can then be activated by PLP in serum or urine. The dipstick reaction can take place in the presence of excess homocysteine or cysteine and of lead acetate which will turn the dipstick black due to the formation of lead sulfide. In another preferred embodiment, the reconstituted holoenzyme regains the ability to hydrolyze homocysteine, producing $H_2S$ in direct relationship to the amount of PLP available.

The apoenzymes may be immobilized on any solid medium by methods known in the art, such as filter paper or beads, appropriate for ease of contact with the sample. The restoration/activation of enzymatic activity may also occur in the presence of appropriate substrate(s) for the holoenzyme to result in the production of enzymatic products that directly reflect the amount of PLP in the sample.

In a preferred embodiment, the invention may be practiced in the presence of excess homocysteine in the case of PLP-free methionine/homocysteine $\alpha,\gamma$-lyase. Additionally, the invention may be practiced using methylene blue derivatives to measure $H_2S$ derived from homocysteine or cysteine; using MBTH to measure $\alpha$-ketobutyrate; utilizing lead acetate to measure $H_2S$; or using dimethyl phenylene diamine (PDA), diethyl PDA, dipropyl PDA or dibutyl PDA to measure $H_2S$. Alternatively, the invention may be practiced by measuring pyruvate derived from excess cysteine utilizing lactate dehydrogenase and NADH; or by measuring ammonia in the presence of excess methionine, homocysteine, or cysteine. When immobilized on filter paper, the invention may also be practiced with an excess of homocysteine or cysteine, and lead acetate to form lead sulfide in the presence of the above lyases.

It is recognized that the total concentration of PLP present in biological samples, for example in body fluids, includes PLP molecules that are not present in free form, being instead covalently coupled to other molecules. The methods of the invention include steps for releasing this PLP prior to measuring. It should be noted, however, that since the methodology of the present invention provides for accurate measurement of free PLP levels, valuable information is provided even if only free PLP is detected. Among many uses, it is expected that such information is very useful as a fast initial diagnostic tool, for example, in an initial testing for Vitamin $B_6$ deficiency.

Depending on the manner of measurement, other sample preparation techniques may be desirable or necessary. For example, for colorometric assays, whole blood should be treated to remove red blood cells. Further fractionation may be desirable as well.

The invention also relates to diagnostic kits containing these apoenzymes, and in particular a homogeneous diagnostic test for Vitamin $B_6$ using a methionine/homocysteine α,γ-lyase or cysteine α,β-lyase, such as those from *Pseudomonas putida* and *Trichomonas vaginalis* and *Pseudomonas ovalis*. These enzymes may be prepared from naturally occurring sources or by recombinant means.

The technical aspects of the invention involve the isolation of methioninase or homocysteinase in which there is sufficient PLP removal to eliminate any activity in the presence of excess methionine or homocysteine. This condition will allow nM levels of $B_6$ to activate the enzyme and give the highly amplified signal as described above. Therefore, the enzyme acts analogously to a transistor or switch to give a highly amplified signal from a very low amount of Vitamin $B_6$.

One PLP requiring enzyme that is preferred in the practice of the invention is L-methionine-alpha-deamino-gamma-mercaptomethane lyase (methionine lyase) derived from the bacterial source, *Pseudomonas putida*. The enzyme has been purified by S. Ito, et al., *Journal of Biochemistry*, (1976) 79, pp. 1263–1272, and determined to have a molecular weight of about 170 kDa. In the context studied by S. Ito, the enzyme carried out the alpha-gamma elimination of methionine to alpha-keto butyrate, methanethiol, and ammonia. If homocysteine is the substrate, then alpha-keto butyrate, hydrogen sulfide, and ammonia are the resultant products. The homologous enzyme has been isolated from *Pseudomonas ovalis*, H. Tanaka, et al., *Biochemistry*, (1977) 16, pp. 100–106. Methods for the recombinant production of this Pseudomonas enzyme have also been developed (see Y. Tan, et al., *Protein Expression and Purification*, (1997) 9, pp. 233–245), and use of recombinant enzyme in the clinical practice of the present invention is expected to provide advantages in terms of diagnostic kit cost and assay reproducibility. The Tan, et al., reference describes construction of a clone designated pAC1-1 containing a single copy of enzyme-encoding sequence. An additional clone, designated pAC1-11, has been constructed which contains two copies of the encoding sequence, in tandem. As with the pAC1-1 structure, the pT7-7 plasmid was used to construct pAC1-11. The two encoding sequences are linked together at a BamHI site, with the first gene linked NdeI to BamHI, and the second linked BamHI to a further BamHI site.

The substrate specificity of the *P. putida* enzyme has also been determined. For example, N. Esaki, et al., *Methods in Enzymology* (1987) 143, pp. 459–465 report that on a relative activity scale where activity toward methionine is assigned 100, cysteine is 10, and homocysteine is 180. The enzyme is thus reactive to all three thiol-containing amino acids. It should be noted that the apparent 10-fold preference of the enzyme for homocysteine over cysteine does not take into account that the concentration of cysteine in a biological sample may be high—in fact is generally much higher than the concentration of homocysteine. PLP requiring enzyme enzymes of suitable catalytic activity can be derived from other Pseudomonas species, or from other bacteria, using routine screening procedures and assays that are recognized in the art.

An additional group of organisms that are a source of PLP requiring enzyme useful in the practice of the invention are species of the Trichomonad parasites and related protozoans. Trichomonads are important parasites of the urogenital tract and are aerotolerant (but nonetheless anaerobic) flagellate protozoa. Use of homocysteinase from *Trichomonas vaginalis* is preferred according to the practice of the invention.

Trichomonas species are believed to use their capabilities for thiol metabolism in order to counter oxygen toxicity in host tissues, see K.-W. Thong, et al., *Experimental Parasitology* (1987) 63, pp. 143–151, and papers cited therein. Although considerable variation in homocysteinase activity (termed homocysteine desulphurase activity therein) was found between Trichomonas species, it is routine to screen available species for acceptable levels of enzyme activity. Generally speaking, it is preferred that a PLP requiring enzyme should have a specific activity of at least about 1 unit/mg purified protein for use in the below-described assays, although it is well within the skill of those familiar with the relevant art to design variations on these assays that use greater or lesser amounts of enzyme or enzyme preparations with differing enzyme activity. It is noted that highly purified and active *P. putida* enzyme has a specific activity of about 20 units/mg (a unit of enzyme activity may be described as 1 micromole of substrate converted per minute under standard conditions (see Y. Tan, et al., above).

The "homocysteine desulphurase activity" reported by K.-W. Thong, et al., (1987) above appears to result from the same enzyme responsible for methionine catabolizing activity in Trichomonas, and later termed methionine-gamma-lyase by B. C. Lockwood and G. H. Coombs (*Biochemical Journal* (1991) 279, pp. 675–682) wherein is also described purification of this enzyme. As aforementioned, use of methionine-gamma-lyase (a homocysteinase) from *Trichomonas vaginalis* is preferred in the practice of the present invention.

Use of a recombinant version of the *T. vaginalis* enzyme is also preferred. One potential cloning strategy follows the observations by A. Marcos, et al., FEMS Microbiology Letters (1996) 135, pp. 259–264, that *T. vaginalis* genes may have few introns. Accordingly, a genomic library would be constructed (see D. E. Riley, et al., *Molecular and Biochemical Parasitology* (1992) 51, pp. 161–164) and screened with DNA fragments corresponding to the *Pseudomonas putida* enzyme, and which are expected to reflect some partially conserved sequence.

Lockwood, et al., also list other reports of bacteria having methionine-gamma-lyase activity involving species of Pseudomonas, Clostridium, and Aeromonas.

It is expected that such species are sources of homocysteinase activity useful in the practice of the present invention. Additional organisms that are expected to provide useful homocysteinase enzymes are certain marine algae (see, for example, D. A. Gage, et al., *Nature* (1997) 387, pp. 891–897), describing species with extensive methionine-related metabolism); sulfur bacteria; and geomicrobes or other microbes living under extreme environmental conditions (see, for example, R. A. Kerr, *Science* (1997) 276, pp. 703–704, and E. Pennist, *Science* (1997) 276, pp. 705–706). Additional examples of microorganisms that may be useful sources for homocysteinase-type enzymes include bacteria involved in periodontal disease, such as are capable of forming volatile sulfur compounds from cysteine. In this regard, see S. Persson, et al., *Oral Microbiology and Immunology* (1990) 5(4), pp. 195–201.

The above-referenced PCT publication WO 99/05311 also describes various forms of homocysteinase which are useful in the methods of the invention. Some of these enzymes are chimeric forms of those isolated from *P. putida* and *T. vaginalis*. The description of suitable enzymes in this publication is incorporated herein by reference.

In addition, the PCT publication WO 99/05311 describes various methods for detecting the products of the holoenzyme. For example, an assay for alpha-ketobutyrate or pyruvate (depending on whether the substrate is homocysteine, methionine or cysteine) is described. The assay uses 3-methyl-2-benzothiazolinone hydrazone (MBTH) to develop a reaction product which can be measured by spectrophotometry at 320 nm. Lead acetate or other lead salts can also be used to detect and measure $H_2S$ produced from homocysteine or cysteine. Further, the ammonia produced in the reaction can be detected using, for example, glutamate dehydrogenase. Methane thiol produced with the substrate is methionine can be determined by production of methylene blue, including variants thereof, by measuring the optical density at about 500 nm using as reactant an N,N-dialkyl p-phenylene diamine. This is described by Tanaka, et al., *J. Applied Biochem* (1980) 2;439–444.

As set forth above, a preferred method for detecting the product of the holoenzyme as a measure of PLP concentration is a chromogenic method wherein the $H_2S$ produced is reacted with an N,N-dialkyl p-phenylene diamine, including the dimethyl, diethyl, dipropyl or dibutyl forms. These compounds are commercially available. The mixture of the N,N-dialkyl phenylene diamine with $H_2S$ is converted to a colored product, 3,7-bis dialkylamino phenylthiazine-5 chloride by treatment with an oxidizing agent such as ferric ion provided by potassium ferricyanide. The resultant compound is measured by optical absorbance at around 675 nm.

An improvement in sensitivity can be obtained by measuring the fluorescence of this product rather than absorbance. Typically, it is subjected to an excitation wavelength of around 640 nm and fluorescence is read at 675 nm. Such an improvement in sensitivity is important when the enzyme is used to assay for the presence of substrate, such as homocysteine. However, although helpful, the increase in sensitivity is not as significant in the formats whereby the analyte is the co-factor PLP since the sensitivity of the assay can be enhanced by increasing the concentration of substrate homocysteine. Example 4, below, shows the advantages of fluorescence assays in the context of an assay for homocysteine.

It will be recognized that the assay of the invention for $PLP/B_6$ can be conducted in a variety of formats. A format whereby the enzyme is supplied on a solid support is described above. However, preferred is a homogeneous assay which offers a simple readout in terms of a spectrophotometric measurement.

Also included in the invention are diagnostic kits for conduct of the PLP assay. In a preferred embodiment, the kit will include the apoenzyme in the form of a recombinant homocysteinase, a standard pyridoxal phosphate sample, chromogenic reagents, preferably N,N-dibutyl p-phenylene diamine, an oxidizing agent such as potassium ferricyanide and the substrate homocysteine. These reagents are packaged in a convenient way, preferably with appropriate buffers for effecting binding of the pyridoxal phosphate in the sample to the apoenzyme and an assay buffer for the conduct of the assay. The binding buffer is preferably slightly acidic in the range of pH 4.5–5.5, preferably around 5–5.2 and the assay buffer is preferably slightly alkaline, preferably pH 7.5–9, more preferably around pH 8.3. A suitable stabilizing reducing agent, such as dithiothreitol and a chealator such as EDTA may also be included.

Suitable kits for conduct of the assay for homocysteine will include the recombinant homocysteinase, a solution of N,N-dialkyl p-phenylene diamine, preferably the di-n-butyl derivative, an oxidizing agent such as potassium ferricyanate, and a reducing agent such as dithiothreitol, or beta mercaptoethanol. It will also contain homocysteine or homocystine as a calibration standard.

All references cited above are hereby incorporated by reference in their entireties, whether or not previously specifically incorporated.

The following examples are intended to illustrate but not to limit the invention.

EXAMPLE 1

Preparation of Apo-Homocysteinase

A mixture was prepared of 1.80 ml of holo-recombinant homocysteinase (rHCYase) solution (3.75 mg protein/ml 20 mM phosphate buffer, pH 7.6), 40 ul of 100 mM dithiothreitol (DTT) and 200 ul of 100 mM hydroxylamine phosphate. The mixture was vortexed and incubated at 4° C. overnight.

The resulting apo-rHCYase was precipitated with 45% ammonium sulfate and centrifuged at 1200 RPM for 10 minutes. The supernatant was discarded and the pellet was dissolved in 1 ml of 20 mM phosphate buffer (pH 7.6). One ml of this solution was loaded onto a 1.0×10-cm G-25 gel filtration column and the column was washed with 20 mM phosphate buffer (pH 7.6). The protein-containing fractions were collected and found to be free of pyridoxal phosphate (PLP). The concentration of protein was adjusted to 0.1 mg protein/ml containing 1.0 mg/ml trehalose.

Analysis confirmed that the apo-rHCYase contained only 0.018±0.002 moles of PLP per subunit (using the same assay, the holoenzyme contains 0.93±0.10 moles PLP per subunit).

EXAMPLE 2

Assay for Pyridoxal Phosphate

A standard curve was prepared by diluting 5 ul of a solution containing various concentrations of PLP into 0.475 ml of binding buffer (10 mM citrate/phosphate buffer pH 5.2, 1 mM EDTA, 0.2 mM DTT), and mixed with 20 ul of the Apo-rHCYase solution prepared as described in Example 1 in assay buffer (200 mM potassium phosphate buffer pH 8.3, 1 mM EDTA, 0.2 mM DTT). The samples were mixed well, and pre-incubated at 37° C. for 120 minutes and protected from light. 50 ul of a solution of DL homocysteine (a concentration) were added to 0.450 ml of assay buffer mixed and added to the above samples, mixed well, and pre-incubated at 37° C. for 20 minutes with protection from light. To this mixture was then added 50 ul of 50 mM di-n-butyl p-phenylene diamine dissolved in 6 M HCl and 50 ul 50 mM potassium ferricyanide dissolved in assay buffer, mixed, and incubated at 37° C. for 10 minutes. The absorbance was then read at 675 nm. The absorbance is linear over the range of 0–200 nM PLP as shown in FIG. 1.

Figure 2:
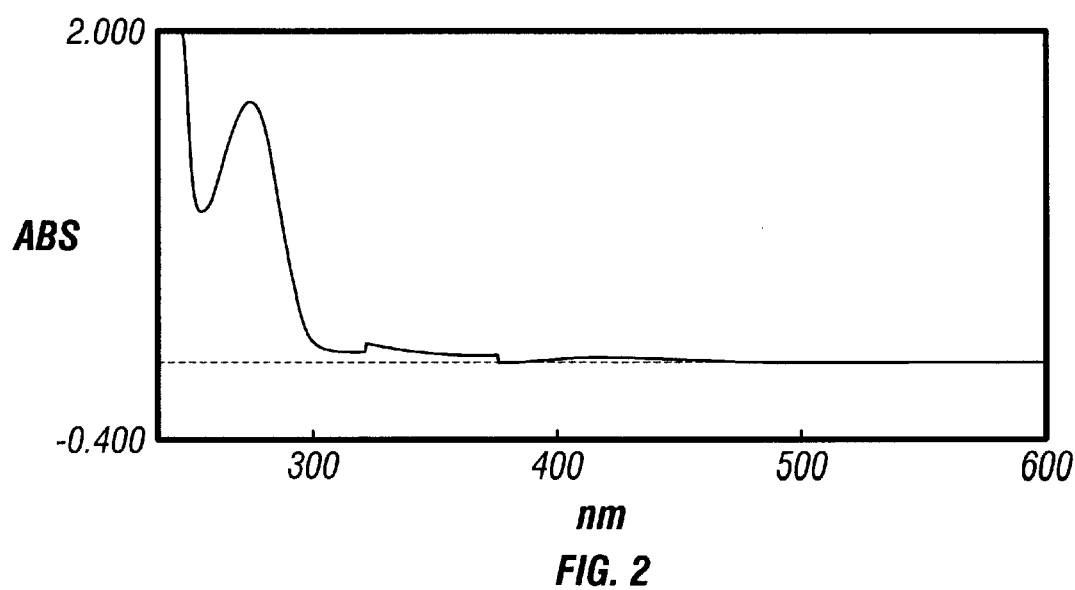
FIG. 2 shows the spectrum of homocysteine alpha, gamma lyase cloned from *Trichomonas vaginalis* after treatment with hydroxylamine.
Figure 3:
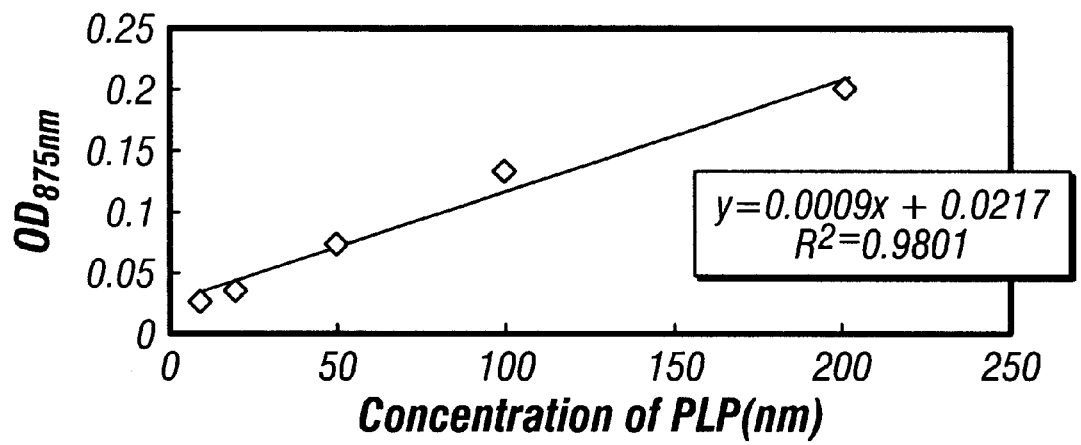
FIG. 3 shows a standard curve determining the concentration of PLP in standards of various concentrations using the colorometric assay of the invention.

The sensitivity of the assay is somewhat enhanced by substituting a fluorescence determination for measurement of optical density at 675. Using the same protocol, but reading the results using an excitation wavelength of 640 nm and an emission wave length of 675 nm the standard curve shown in FIG. 2 is obtained. A comparison of these results in shown in FIG. 3. In both cases, a linear curve is obtained; using fluorescence emission, a reading of 110 fluorescence units is obtained at a concentration of 100 nM; using absorbance a reading of 0.25 OD (approximately) is obtained at 675 nm.

EXAMPLE 3

Determination of PLP in Human Plasma

Figure 4:
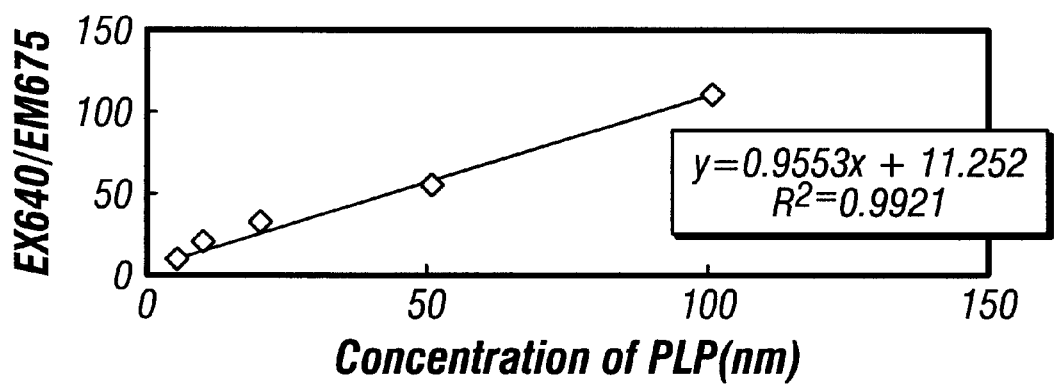
FIG. 4 shows similar results substituting fluorescence measurements for colorometric measurements.
Figure 5:
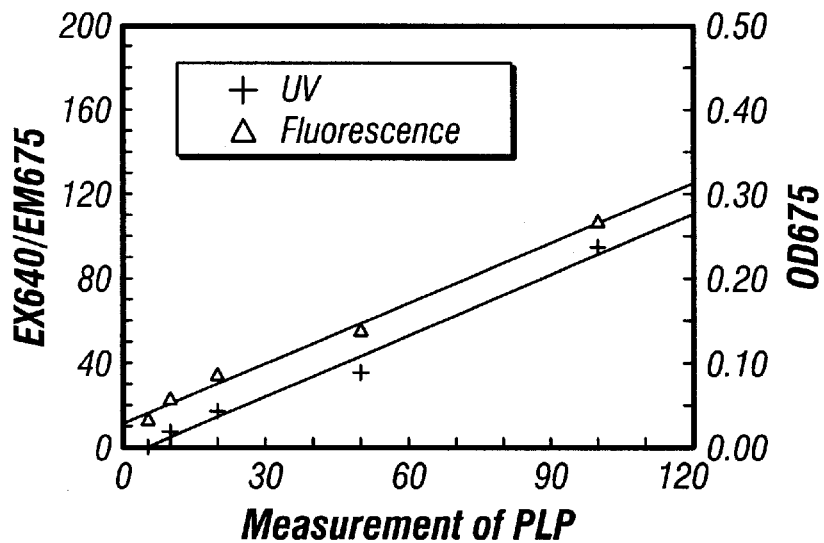
FIG. 5 shows a comparison of the results using colorometric or fluorometric detection means.
Figure 6:
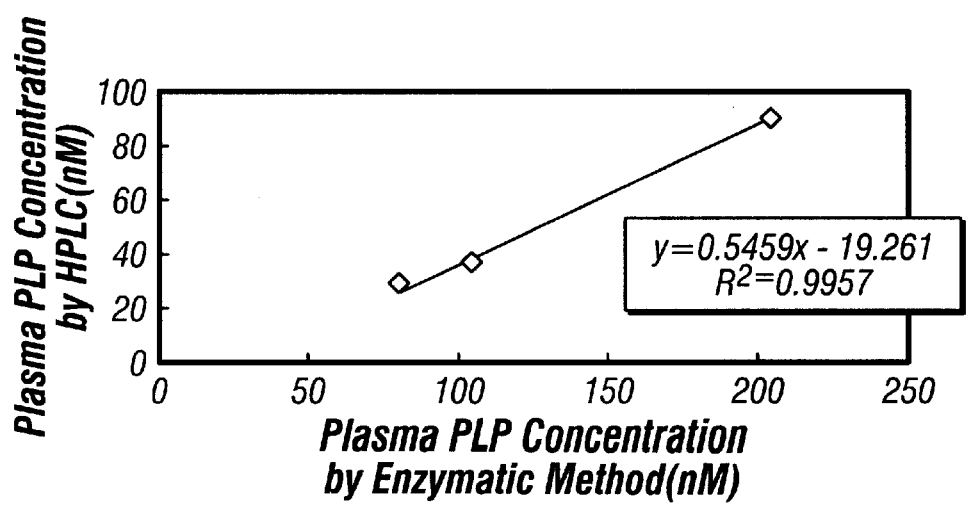
FIG. 6 shows the results of determination of PLP in the plasma of three subjects using the method of the invention as compared to such determination by HPLC.

The procedure of Example 2 was repeated but substituting for the 5 ul of standard solution containing PLP, 5 ul of EDTA treated plasma. The results for three individuals are shown in FIG. 4. The results are shown in comparison to a determination of PLP using the method of HPLC as described in *J. Chromatog* (1996) 722:295–301. As shown in FIG. 4, although the absolute values obtained by the method of the invention differ from those obtained by HPLC, they stand in a linear relationship to each other. However, there is good agreement with results obtained using the apotyrosine carboxylase assay of the ALPCO kit:

| Sample | Invention Method | ALPCO Method |
| --- | --- | --- |
| 1 | 248 nM | 223, nM |
| 2 | 62 nM | 54 nM |

EXAMPLE 4

Determination of Homocysteine Using a Fluorescence Detection Method

By using fluorescence to determine the concentration of the resulting chromophore in a homocysteine assay, the sensitivity can be enhanced approximately 1000-fold in comparison to the sensitivity using absorbance. Therefore, smaller samples, about 10 to 100 fold smaller, can be analyzed using the more sensitive fluorescence-based determination than the absorbance-based determination described above. For example a blood sample derived from finger pricking is sufficient to achieve a strong fluorescence signal in the homocysteine assay.

Figure 7:
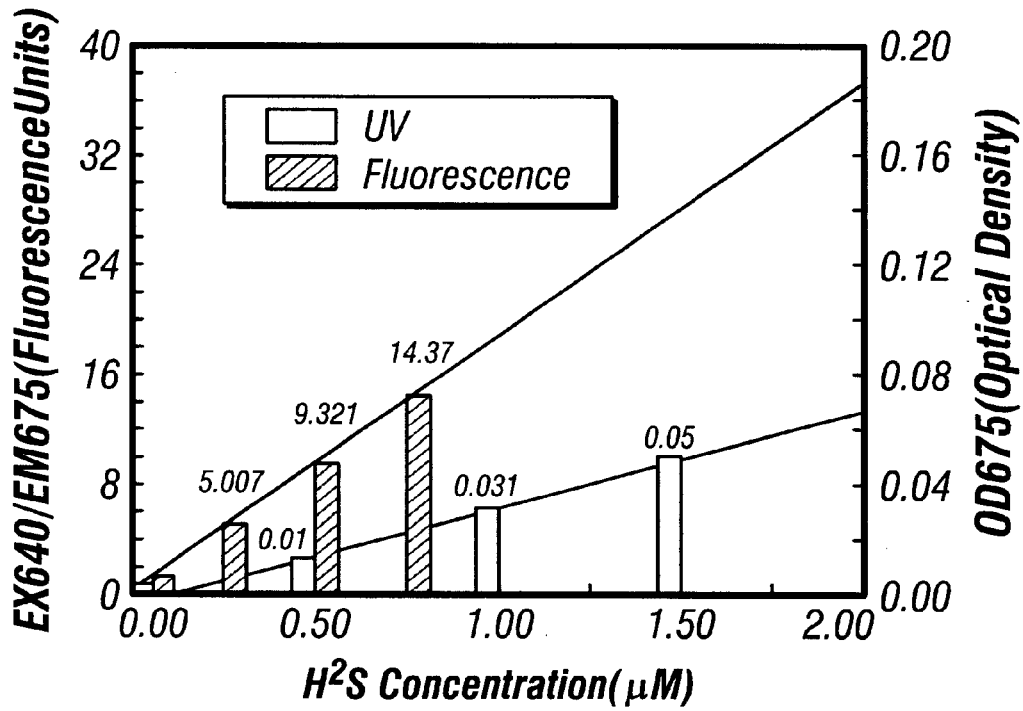
FIG. 7 shows a comparison of fluorescence and ultraviolet absorption of a chromogenic product at various hydrogen sulfide concentrations.

The increased sensitivity of the fluorescence-based assay in comparison to the absorbance-based assay is shown in FIG. 7. In this figure, the X axis represents the hydrogen sulfide concentration in the assay. The steeper curve for the fluorescence signal than for the absorbance signal for the same assay having varying concentrations demonstrates that the fluorescence signal is much more sensitive than the absorbance signal.

Any suitable reagent that provides a proper signal when measured by fluorescence is appropriate. For example, the chromogenic reagent, N,N-dibutyl-p-phenylene-diamine (DBPDA), used for absorbance as discussed above was used in the fluorescence-based assay illustrated in FIG. 7. Generally, the same conditions used for the absorbance-based assays can be used for the fluorescence-based assays, except the assays are measured by fluorescence.

A very strong signal by fluorescence can be obtained using an appropriate combination of excitation and emission wavelengths, which can be determined by one having ordinary skill in the art. For example, excitation at 665 nm and emission at 690 nm, or excitation at 640 nm and emission at 675 can be used under certain conditions.

Figure 8:
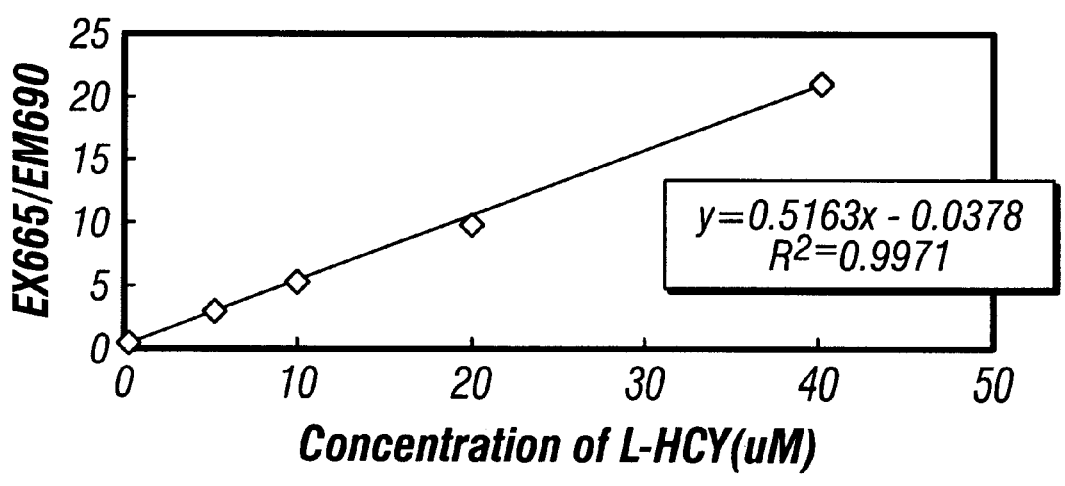
FIG. 8 shows a standard curve of L-homocysteine determined by fluorescence.
Figure 9:
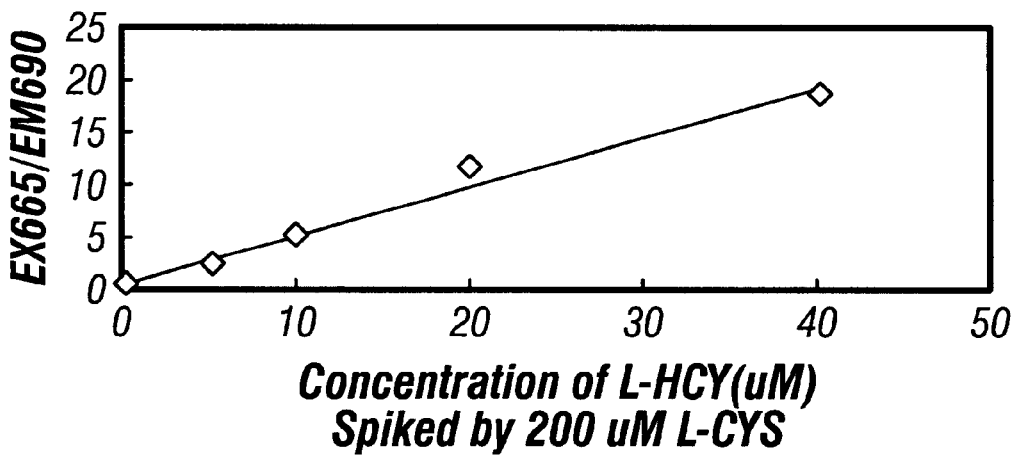
FIG. 9 shows a curve of homocysteine demonstrating the relative lack of interference by cysteine in an enzymatic homocysteine assay measured by fluorescence and results of a blood sample derived from finger pricking.
Figure 10:
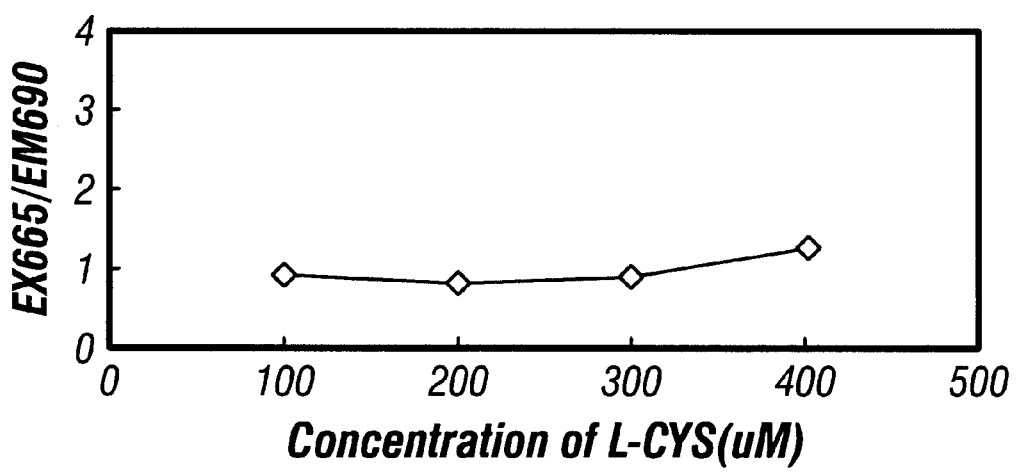
FIG. 10 shows the relative lack of interference by cysteine measured by fluorescence at various concentrations of cysteine.

A comparison of the FIG. 8 standard curve for homocysteine, based on measurements by fluorescence, and the FIG. 9 curve for homocysteine samples that also contain a fixed amount of cysteine, shows that cysteine has minimal interference with the homocysteine measurement. These results are consistent with absorbance-based assays. FIG. 10 shows the relative lack of interference by cysteine samples of varying concentrations.

A small sample of blood derived from finger pricking was used to determine the homocysteine concentration therein. Corresponding the fluorescence readout of the sample with the appropriate concentration in the standard curve in FIG. 8 gave the concentration shown in the results in the chart in FIG. 8.

What is claimed is:

1. A method to determine the concentration of pyridoxal-5'-phosphate (PLP) in a biological sample which method comprises
   (a) incubating said biological sample or a fraction thereof with an apoenzyme form of PLP-dependent homocysteinase, methioninase or cysteinase in the presence of sufficient substrate to effect conversion of said substrate to a spectrophotometrically observable product whose concentration is proportional to the concentration of PLP in the sample;
   (b) detecting the concentration of product spectrophotometrically; and
   (c) correlating said concentration of product with the concentration of PLP in the sample.

2. The method of claim 1 wherein said spectrophotometric detecting is by visualizing with the naked eye.

3. The method of claim 1 wherein the detected product is hydrogen sulfide.

4. The method of claim 3 wherein said hydrogen sulfide is detected by reaction with N,N-dialkyl p-phenylene diamine and an oxidizing agent.

5. The method of claim 4 wherein said product is detected by fluorescence.

6. The method of claim 3 wherein said hydrogen sulfide is detected by observing the precipitation of said hydrogen sulfide with lead ion.

7. The method of claim 1 wherein the apoenzyme is a homocysteinase.

8. A method to determine the concentration of pyridoxal-5'-phosphate (PLP) in a biological sample which method comprises detecting the concentration of a spectrophotometrically detectable product spectrophotometrically, and correlating the concentration of the spectrophotometrically detectable product with the concentration of PLP in the sample, wherein said product is obtained by incubating said biological sample or a fraction thereof with the apoenzyme form of PLP-dependent homocysteinase, methioninase or cysteinase in the presence of sufficient substrate to effect conversion to said spectrophotometrically observable product proportional to the concentration of PLP in the sample.

9. The method of claim 8 wherein said spectrophotometric detecting is by visualizing with the naked eye.

10. The method of claim 8 wherein the detected product is hydrogen sulfide.

11. The method of claim 10 wherein said hydrogen sulfide is detected by reaction with N,N-dialkyl p-phenylene diamine and an oxidizing agent.

12. The method of claim 11 wherein said product is detected by fluorescence.

13. The method of claim 10 wherein said hydrogen sulfide is detected by observing the precipitation of said hydrogen sulfide with lead ion.

14. The method of claim 8 wherein the apoenzyme is a homocysteinase.

15. An isolated apoenzyme form of methioninase, homocysteinase or cysteinase.

16. The apoenzyme of claim 15 wherein said apoenzyme form is coupled to a solid support.

17. A method to improve the sensitivity of an assay which is measured by production of hydrogen sulfide wherein the improvement comprises detecting fluorescence of a resultant obtained by reacting said hydrogen sulfide with an N,N-dialkyl p-phenylene diamine and an oxidizing agent.

18. The method of claim 17 wherein said assay is an assay for homocysteine.

19. A kit for the assay of PLP in a biological fluid which comprises the apoenzyme of claim 15.

20. The kit of claim 19 which further comprises an N,N-dialkyl p-phenylene diamine and an oxidizing agent.

\* \* \* \* \*